(12) United States Patent
Preminger

(10) Patent No.: US 9,993,190 B2
(45) Date of Patent: Jun. 12, 2018

(54) SYSTEM AND METHOD FOR NEUROCOGNITIVE TRAINING AND/OR NEUROPSYCHOLOGICAL ASSESSMENT

(75) Inventor: Son Preminger, Arsuf Kedem (IL)

(73) Assignee: INTENDU LTD., Arsuf Kedem (IL)

( * ) Notice: Subject to any disclaimer, the term of this patent is extended or adjusted under 35 U.S.C. 154(b) by 1110 days.

(21) Appl. No.: 13/586,336

(22) Filed: Aug. 15, 2012

(65) Prior Publication Data

US 2013/0046206 A1  Feb. 21, 2013

Related U.S. Application Data

(60) Provisional application No. 61/523,857, filed on Aug. 16, 2011.

(51) Int. Cl.
| | |
|---|---|
| *A61B 5/16* | (2006.01) |
| *G09B 7/02* | (2006.01) |
| *G09B 19/00* | (2006.01) |
| *A61B 5/00* | (2006.01) |
| *A61B 5/0476* | (2006.01) |

(52) U.S. Cl.
CPC .............. *A61B 5/16* (2013.01); *A61B 5/486* (2013.01); *G09B 7/02* (2013.01); *G09B 19/00* (2013.01); *A61B 5/0476* (2013.01); *A61B 5/6806* (2013.01); *A61B 5/744* (2013.01)

(58) Field of Classification Search
CPC ..................................................... A61B 5/00
See application file for complete search history.

(56) References Cited

U.S. PATENT DOCUMENTS

| | | | |
|---|---|---|---|
| 5,711,671 A | 1/1998 | Geeslin | |
| 5,724,987 A * | 3/1998 | Gevins | ............... A61B 5/0484 434/258 |
| 6,165,126 A | 12/2000 | Merzenich | |
| 6,231,344 B1 | 5/2001 | Merzenich | |
| 6,293,801 B1 | 9/2001 | Jenkins | |
| 6,632,174 B1 * | 10/2003 | Breznitz | ............... A61B 5/16 434/236 |
| 7,024,398 B2 | 4/2006 | Kilgard | |

(Continued)

OTHER PUBLICATIONS

Achtman R.L., Green C.S., Bavelier D (2008) Video games as a tool to train visual skills. Restorative Neurology and Neuroscience 26, 435-446.

(Continued)

*Primary Examiner* — Daniel Cerioni
*Assistant Examiner* — Yasmeen S Warsi
(74) *Attorney, Agent, or Firm* — Browdy and Neimark, PLLC

(57) ABSTRACT

A method of neurocognitive training or neuropsychological assessment of a subject including providing at least one initial stimulus to the subject, assessing at least one initial action of the subject in response to the at least one initial stimulus, based on the assessing the at least one initial action of the subject in response to the at least one initial stimulus, thereafter providing at least one further stimulus to the subject, assessing at least one further action of the subject in response to the at least one further stimulus and based at least on the assessing the at least one further action of the subject in response to the at least one further stimulus, thereafter providing at least one additional stimulus to the subject.

29 Claims, 7 Drawing Sheets

(56) References Cited

U.S. PATENT DOCUMENTS

| | | | |
|---|---|---|---|
| 7,574,254 B2* | 8/2009 | Milgramm | A61B 5/048 600/300 |
| 7,773,097 B2 | 8/2010 | Merzenich | |
| 7,887,329 B2 | 2/2011 | Greenshpan | |
| 2005/0019734 A1 | 1/2005 | Peled | |
| 2005/0216243 A1* | 9/2005 | Graham | G06F 19/3437 703/11 |
| 2007/0166675 A1* | 7/2007 | Atkins | G09B 5/06 434/236 |
| 2007/0166676 A1 | 7/2007 | Bird | |
| 2007/0218439 A1 | 9/2007 | Delahunt | |
| 2007/0298883 A1 | 12/2007 | Feldman | |
| 2007/0299319 A1 | 12/2007 | Chan | |
| 2008/0003558 A1 | 1/2008 | Chan | |
| 2009/0130640 A1 | 5/2009 | Hardy | |
| 2010/0041001 A1 | 2/2010 | Delahunt | |
| 2011/0304632 A1* | 12/2011 | Evertt | G06F 3/011 345/474 |

OTHER PUBLICATIONS

Bialystok, E. (2006) Effect of Bilingualism and Computer Video Game Experience on the Simon Task. Canadian Journal of Experimental Psychology, 60, 1, p. 68.
Boot, W. R., Kramer, A. F., Simons, D. J., Fabiani, M., & Gratton, G.(2008). The effects of video game playing on attention, memory, and executive control. Acta Psychologica, 129, 387-398.
Chein J. M., Morrison a. B. (2010) Expanding the minds workspace. Training and transfer effects with a complex working memory span task. Psychonomic Bulletin & Review, 17 (2), pp. 193-199.
Dorval, M., and M. Pepin. 1986. Effect of playing a video game on a measure of spatial visualization. Perceptual Motor Skills 62, p. 159-162.
Dux P. E. et al. Training improves multitasking performance by increasing the speed of information processing in human prefrontal cortex. Neuron 63 , 127-138, Jul. 2009.
Green C. S. Pouget A., and Bavelier D. (2010) Improved Probabilistic Inference as a General Learning Mechanism with Action Video Games. Current Biology 20, 1573-1579.
Green C. S., Bavelier D (2008). Exercising Your Brain. A Review of Human Brain Plasticity and Training-Induced Learning. Psychology and Aging vol. 23, No. 4, 692-701.
Green C. S., Bavelier D. (2003) Action video game modifies visual selective attention. Nature 423(6939), pp. 534-537.
Green C. S., Bavelier D. (2006b) Effects of action video game playing on the spatial distribution of visuospatial attention. J Exp Psychol Hum Percept Perform, 321465-1478.
Green, C. S., Bavelier, D. (2006a). The cognitive neuroscience of video games. In P. Messaris & L. Humphreys (Eds.), Digital media, Transformations in human communication ( 211-224).
I Z. and DiCarlo J.J. (2006) Current Opinion in Neurobiology,16, 1-7. Learning and neural plasticity in visual object recognition.
Jancke L. (2009) The plastic human brain. Restorative Neurology and Neuroscience 27(5), p. 521-538.
Karni A. and Sagi D. (1991) Where practice makes perfect in texture discrimination. Evidence for primary visual cortex plasticity. Proceedings of National Academy of Science USA, 88, p. 4966-4970.
Karni A. et al (1998). The acquisition of skilled motor performance. fast and slow experience-driven changes in primary motor cortex. Proceedings of National Academy of Science USA, 95, p. 861-868.
Kueider AM, Parisi JM, Gross AL, Rebok GW (2012) Computerized Cognitive Training with Older Adults—A Systematic Review. PLoS ONE 7(7); Jul. 2012, vol. 7, Issue 7.
Kueider AM, Parisi JM, Gross AL, Rebok GW (2012) Computerized Cognitive Training with Older Adults—A Systematic Review. PLoS ONE 7(7).
Li, R., Polat, U., Makous, W., Bavelier, D. (2009). Enhancing the contrast sensitivity function through action video, Nature Neuroscience, 12, 5, 549-551.
Maged, N., Boulos, K. (2012). Xbox 360 Kinect Exergames for Health. Games for Health Journal—Research, Development, and Clinical Applications, 1, 5, 326-330.
Mahncke H.W. et al (2006) Memory enhancement in healthy older adults using a brain plasticity-based training program. Proceedings of National Academy of Science USA 103(33) Aug. 2006 vol. 103 No. 33.
Olesen, P., Westerberg, H., Klingberg, T. (2004). Increased Prefrontal and Parietal Activity after Training of Working Memory. Nature Neuroscience, 7, 1, 75-79.
OS. M., Buschkuehl M., JonidesJ. and Perrig W.J. Improving fluid intelligence with training on working memory. PNAS 2008 (105), pp. 6829-6833.
Owen A. M. et al. Putting brain training to the test. Nature 2010, 465, pp. 775-778.
Pascual-Leone A.; Amedi A.; Fregni F.; Merabet L. B. (2005) The Plastic Human Brain Cortex. Annual Review Neuroscience 28, p. 377-401.
Polat U., Ma-Naim T., Belkin M. and Sagi D. (2004) Improving vision in adult amblyopia by perceptual learning. Proceedings of National Academy of Science USA, 101, p. 6692-6697.
Preminger S., Blumenfeld B., Sagi D, Tsodyks M.(2009b). Mapping Memories of Gradually Changing Objects. Proceedings of National Academy of Science USA, 106, p. 5371-5376.
Preminger S., Sagi D., Tsodyks M. (2007). Effects of Perceptual History on Memory of Visual Objects. Vision Research 47, p. 965-973.
Preminger, S. (2009). Improvisation for Neurorehabilitation. Frontiers in Neuroscience, May 2009 vol. 3 Issue 1.
Preminger, S. (2011) Improvisation for Prefrontal Rehabilitation. Chapter 2 in Augmenting Cognition, by EPFL Press Switzerland (edited by Henry Markram and Idan Segev)_.
Preminger, S. (2012). Transformative art—art as means for long-term neurocognitive change. Frontiers in Human Neuroscience, 6, 96, 1-6.
Prins, P.J.M. (2013). "Braingame Brian": Toward an Executive Function Training Program with Game Elements for Children with ADHD and Cognitive Control Problems. Games for Health Journal: Research, Development, and Clinical Applications, 2,1, 44-49.
Sagi D. (2011) Perceptual learning in Vision Research. Vision Research 51(13), p. 1552-1566.
Subramaniam, K. et al. (2012) Computerized Cognitive Training Restores Neural Activity within the Reality Monitoring Network in Schizophrenia. Neuron, 73, 842_853.
Takeuchi, H. et al (2010). Training of Working Memory Impacts Structural Connectivity. The Journal of Neuroscience, 30(9) 3297-3303.
Thorell L. B., Lindqvist S., Nutley S. B., Bohlin G. and Klingberg T. Training and transfer effects of executive functions in preschool children. Dev. Sci. 2009, 12, pp. 106-113.
Willis S. L., et al. Long-term Effects of Cognitive Training on Everyday Functional Outcomes in Older Adults. JAMA. 2006, 296, pp. 2805-2814.

\* cited by examiner

SYSTEM AND METHOD FOR NEUROCOGNITIVE TRAINING AND/OR NEUROPSYCHOLOGICAL ASSESSMENT

REFERENCE TO RELATED APPLICATIONS

Reference is hereby made to U.S. Provisional Patent Application 61/523,857, filed Aug. 16, 2011 and entitled Neurocognitive assessment and training based on naturalistic interaction and environments, which are personally adjusted based on user' behavior and neurofeedback, priority of which is hereby claimed pursuant to 37 CFR 1.78(a)(4) and (5)(i).

FIELD OF THE INVENTION

The present invention relates to systems and methodologies for neurocognitive training and neuropsychological assessment.

BACKGROUND OF THE INVENTION

Various systems and methodologies exist for neurocognitive interaction. Examples of the type of systems and methodologies that are presently known in the literature include the following:

Polat U., Ma-Naim T., Belkin M. and Sagi D. (2004): Improving vision in adult amblyopia by perceptual learning. Proceedings of National Academy of Science USA, 101, p. 6692-6697;

JaeggiS. M., Buschkuehl M., Jonides J. and Perrig W. J. Improving fluid intelligence with training on working memory. PNAS 2008 (105), pp. 6829-6833;

Dux P. E.; Tombu M. N.; Harrison S., Rogers B. P., Tong F. and Marois R.: Training improves multitasking performance by increasing the speed of information processing in human prefrontal cortex. Neuron 2009, 63(1), pp. 127-138;

Willis S. L., et al. Long-term Effects of Cognitive Training on Everyday Functional Outcomes in Older Adults. JAMA. 2006, 296, pp. 2805-2814;

Thorell L. B., Lindqvist S., Nutley S. B., Bohlin G. and Klingberg T.: Training and transfer effects of executive functions in preschool children. Dev. Sci. 2009, 12, pp. 106-113;

Mahncke H. W., Connor B. B., Appelman J., Ahsanuddin O. N., Hardy J. L., Wood R. A., Joyce M. N., Boniske T., Atkins S. M., and Merzenich M. M. (2006): Memory enhancement in healthy older adults using a brain plasticity-based training program: A randomized, controlled study. Proceedings of National Academy of Science USA 103(33), p. 12523-12528;

Owen A. M. et al. Putting brain training to the test. Nature 2010, 465, pp. 775-778;

Chein J. M., Morrison A. B. (2010) Expanding the mind's workspace: Training and transfer effects with a complex working memory span task. Psychonomic Bulletin & Review, 17 (2), pp. 193-199;

Karni A., Meyer G., Rey-Hipolito C., Jezzard P., Adams M. M., Turner R. and Ungerleider L. G. (1998). The acquisition of skilled motor performance: fast and slow experience-driven changes in primary motor cortex. Proceedings of National Academy of Science USA, 95, p. 861-868;

Karni A. and Sagi D. (1991) Where practice makes perfect in texture discrimination: Evidence for primary visual cortex plasticity. Proceedings of National Academy of Science USA, 88, p. 4966-4970;

Kourtzi Z. and DiCarlo J. J. (2006) Current Opinion in Neurobiology, 16:1-7. Learning and neural plasticity in visual object recognition;

Jancke L. (2009) The plastic human brain. Restorative Neurology and Neuroscience 27(5), p. 521-538;

Pascual-Leone A.; Amedi A.; Fregni F.; Merabet L. B. (2005) The Plastic Human Brain Cortex. Annual Review Neuroscience 28, p. 377-401;

Sagi D. (2010) Perceptual learning in Vision Research. Vision Research 51(13), p. 1552-1566;

Kueider A M, Parisi J M, Gross A L, Rebok G W (2012) Computerized Cognitive Training with Older Adults: A Systematic Review. PLoS ONE 7(7);

Achtman R. L., Green C. S., Bavelier D (2008) Video games as a tool to train visual skills. Restorative Neurology and Neuroscience 26, 435-446;

Boot, W. R., Kramer, A. F., Simons, D. J., Fabiani, M., & Gratton, G. (2008). The effects of video game playing on attention, memory, and executive control. Acta Psychologica, 129, 387-398;

Dorval, M., and M. Pepin. 1986. Effect of playing a video game on a measure of spatial visualization. Perceptual Motor Skills 62, p. 159-162;

Green C. S. Pouget A., and Bavelier D. (2010) Improved Probabilistic Inference as a General Learning Mechanism with Action Video Games. Current Biology 20, 1573-1579;

Green C. S., Bavelier D (2008). Exercising Your Brain: A Review of Human Brain Plasticity and Training-Induced Learning. Psychology and Aging Vol. 23, No. 4, 692-701;

Green, C. S., Bavelier, D. (2006a). The cognitive neuroscience of video games. In P. Messaris & L. Humphreys (Eds.), Digital media: Transformations in human communication (pp. 211-224). New York: Peter Lang;

Green C. S., Bavelier D. (2006b) Effects of action video game playing on the spatial distribution of visual selective attention. J Exp Psychol Hum Percept Perform, 32:1465-1478;

Green C. S., Bavelier D. (2003) Action video game modifies visual selective attention. Nature 423(6939), pp. 534-7;

Preminger S. (2011) Improvisation for Prefrontal Rehabilitation. Chapter 2 in Augmenting Cognition, by EPFL Press Switzerland (edited by Henry Markram and Idan Segev);

Improvisation for Neurorehabilitation. Frontiers in Neuroscience, special issue on Augmenting Cognition;

Preminger S., Blumenfeld B., Sagi D, Tsodyks M. (2009b). Mapping Memories of Gradually Changing Objects. Proceedings of National Academy of Science USA, 106, p. 5371-6;

Preminger S., Sagi D., Tsodyks M. (2007). Effects of Perceptual History on Memory of Visual Objects. Vision Research 47, p. 965-973;

U.S. Pat. Nos. 5,711,671; 5,724,987; 6,165,126; 6,231,344; 6,293,801; 6,632,174; 7,024,398; 7,773,097 and 7,887,329; and U.S. Published Patent Application Nos.: 2005/0019734; 2007/0218439; 2007/0166675; 2007/0166676; 2007/0299319; 2008/0003558; 2007/0298883; 2009/0130640 and 2010/0041001.

The following products also provide neurocognitive interaction.

"Kinectimals" commercially available from Microsoft studios, Microsoft Corporation;

"Kinect Star Wars" commercially available from Microsoft studios, Microsoft Corporation;

"Kinect Adventures" commercially available from Microsoft studios, Microsoft Corporation;

"Kinect Sports" commercially available from Microsoft studios, Microsoft Corporation;

"Dance Central" commercially available from MTV Games, MTV;

"MotionSports" commercially available from Ubisoft Entertainment;

"Body and Brain Connection" commercially available from Namco Bandai Games America Inc.;

"Rise of Nightmares" commercially available from Sega Corporation;

"Lumosity" commercially available from Lomus Labs Inc.;

"MindFit" commercially available from CogniFit Ltd.;

"Brain Fitness Program" commercially available from Posit Science Inc.; and

"Brain Fitness" commercially available from Dakim Inc.

SUMMARY OF THE INVENTION

The present invention seeks to provide improved systems and methodologies for neurocognitive interaction generally and more particularly improved systems and methodologies for neurocognitive assessment and training.

There is thus provided in accordance with a preferred embodiment of the present invention a method of neurocognitive training or neuropsychological assessment of a subject including the steps of providing at least one initial stimulus to the subject, assessing at least one initial action of the subject in response to the at least one initial stimulus, the at least one initial action being at least one of absence, presence, timing and/or form of at least one of body movements, vocal expressions and facial expressions, based on the assessing the at least one initial action of the subject in response to the at least one initial stimulus, thereafter providing at least one further stimulus to the subject, assessing at least one further action of the subject in response to the at least one further stimulus, the at least one further action being at least one of absence, presence, timing and/or form of at least one of body movements, vocal expressions and facial expressions and based at least on the assessing the at least one further action of the subject in response to the at least one further stimulus, thereafter providing at least one additional stimulus to the subject.

Preferably, the assessing employs at least one of neurofeedback and biofeedback.

In accordance with a preferred embodiment of the present invention the at least one further stimulus differs from the at least one initial stimulus in at least one of the following respects: a. the number, duration, timing and/or order of the stimuli, b. the context in which the stimuli are provided, the type of stimuli, d. the view which characterizes how the stimuli are experienced, e. the representation of the subject in the stimuli, f. the makeup of the environment of the stimuli, g. the representation of the actions of the subject in the stimuli, h. the representation of the actions of the subject on the external virtual environment; i. aggressiveness of the stimuli, j. extent of interactivity in a scenario initiated by the stimuli and k. the representation of one or more physical objects in the stimuli, which objects can be manipulated by the subject. More preferably, the at least one further stimulus differs from the at least one initial stimulus in at least five of the respects a-k. Most preferably, the at least one further stimulus differs from the at least one initial stimulus in all of the respects a-k.

Preferably, at least one of the type and extent of subject activity in response to the at least one initial stimulus which will elicit a given at least one further stimulus is variable.

There is also provided in accordance with another preferred embodiment of the present invention a method of neurocognitive training or neuropsychological assessment of a subject including the steps of: providing at least one initial stimulus to the subject, assessing at least one initial action of the subject in response to the at least one initial stimulus, based on the assessing the at least one initial action of the subject in response to the at least one initial stimulus, thereafter providing at least one further stimulus to the subject, the at least one further stimulus differing from the at least one initial stimulus in respect of at least one of: a view which characterizes how the at least one further stimulus is experienced, a representation of the subject in an avatar in the at least one further stimulus, a representation of at least one action of the subject in the avatar in the at least one further stimulus and a representation of at least one action of the subject on an external virtual environment context of the at least one further stimulus.

Preferably, the assessing employs at least one of neurofeedback and biofeedback.

In accordance with a preferred embodiment of the present invention the at least one further stimulus also differs from the at least one initial stimulus in at least one of the following respects: the number, duration, timing and/or order of the stimuli, the context in which the stimuli are provided, the type of stimuli, the makeup of the environment of the stimuli, aggressiveness of the stimuli, extent of interactivity in a scenario initiated by the stimuli and the representation of one or more physical objects in the stimuli, which objects can be manipulated by the subject. Alternatively, the at least one further stimulus also differs from the at least one initial stimulus in all of the following respects: the number, duration, timing and/or order of the stimuli, the context in which the stimuli are provided, the type of stimuli, the makeup of the environment of the stimuli, aggressiveness of the stimuli, extent of interactivity in a scenario initiated by the stimuli and the representation of one or more physical objects in the stimuli, which objects can be manipulated by the subject.

Preferably, at least one of the type and extent of subject activity in response to the at least one initial stimulus which will elicit a given at least one further stimulus is variable.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

The present invention provides a system and method for neurocognitive training or neuropsychological assessment of a subject including functionality which provides at least one initial stimulus to a subject, assesses at least one initial action of the subject in response to the at least one initial stimulus, the action being the absence, presence, timing and/or form of at least one of body movements, vocal and facial expressions, based on the assessment of the at least one initial action of the subject in response to the at least one initial stimulus, thereafter provides at least one further stimulus to the subject, assesses at least one further action of the subject in response to the at least one further stimulus, the action being the absence, presence, timing and form of at least one of body movements, vocal and facial expressions and based at least on the assessment of the at least one further action of the subject in response to the at least one further stimulus, thereafter providing at least one additional stimulus to the subject.

Figure 1A:
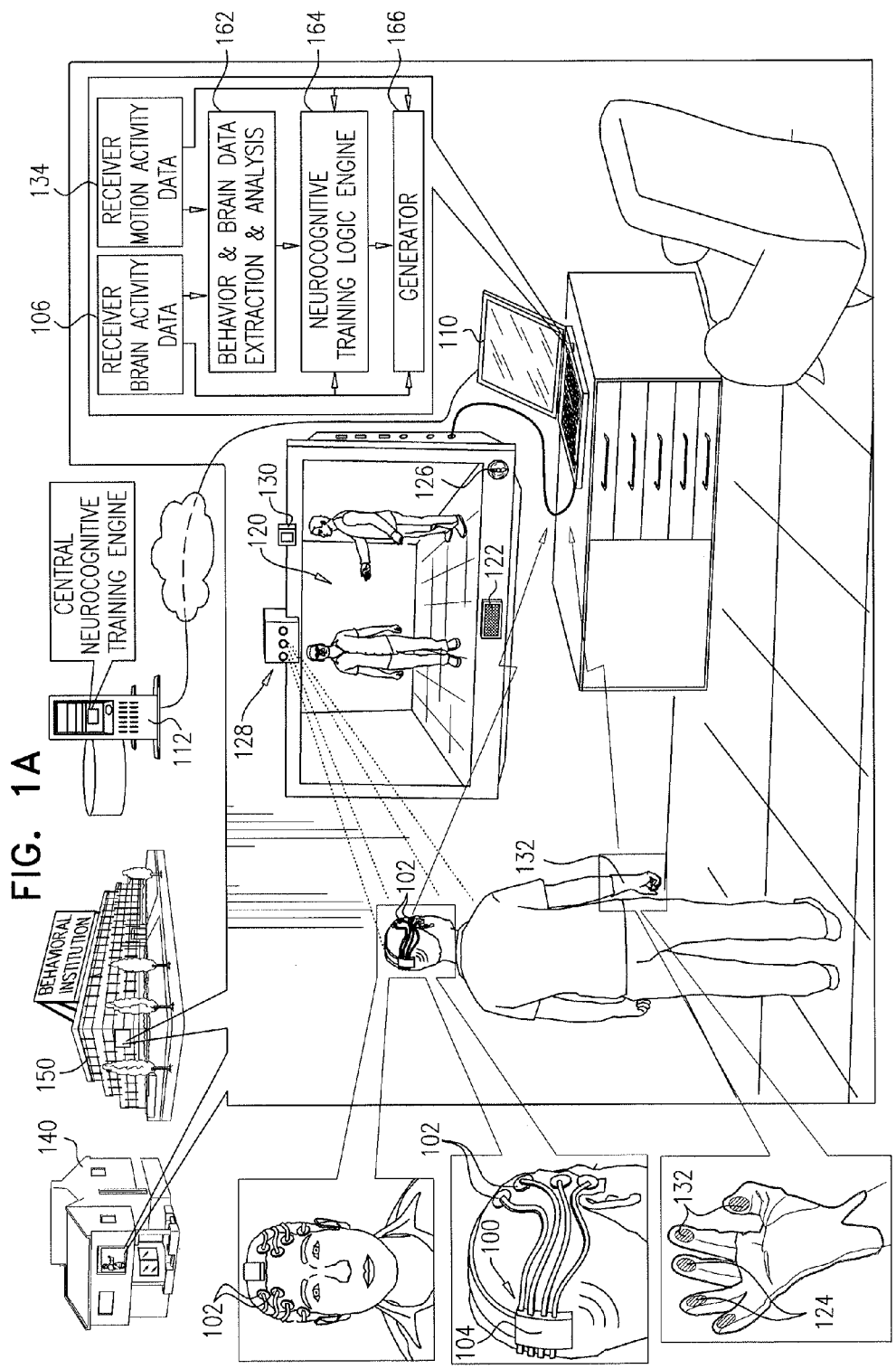
FIGS. 1A, 1B and 1C are together a simplified illustration of a first typical scenario in the operation of systems and methodologies for neurocognitive interaction, which may be used for neurocognitive assessment and/or training, constructed and operative in accordance with a preferred embodiment of the present invention.
Figure 1B:
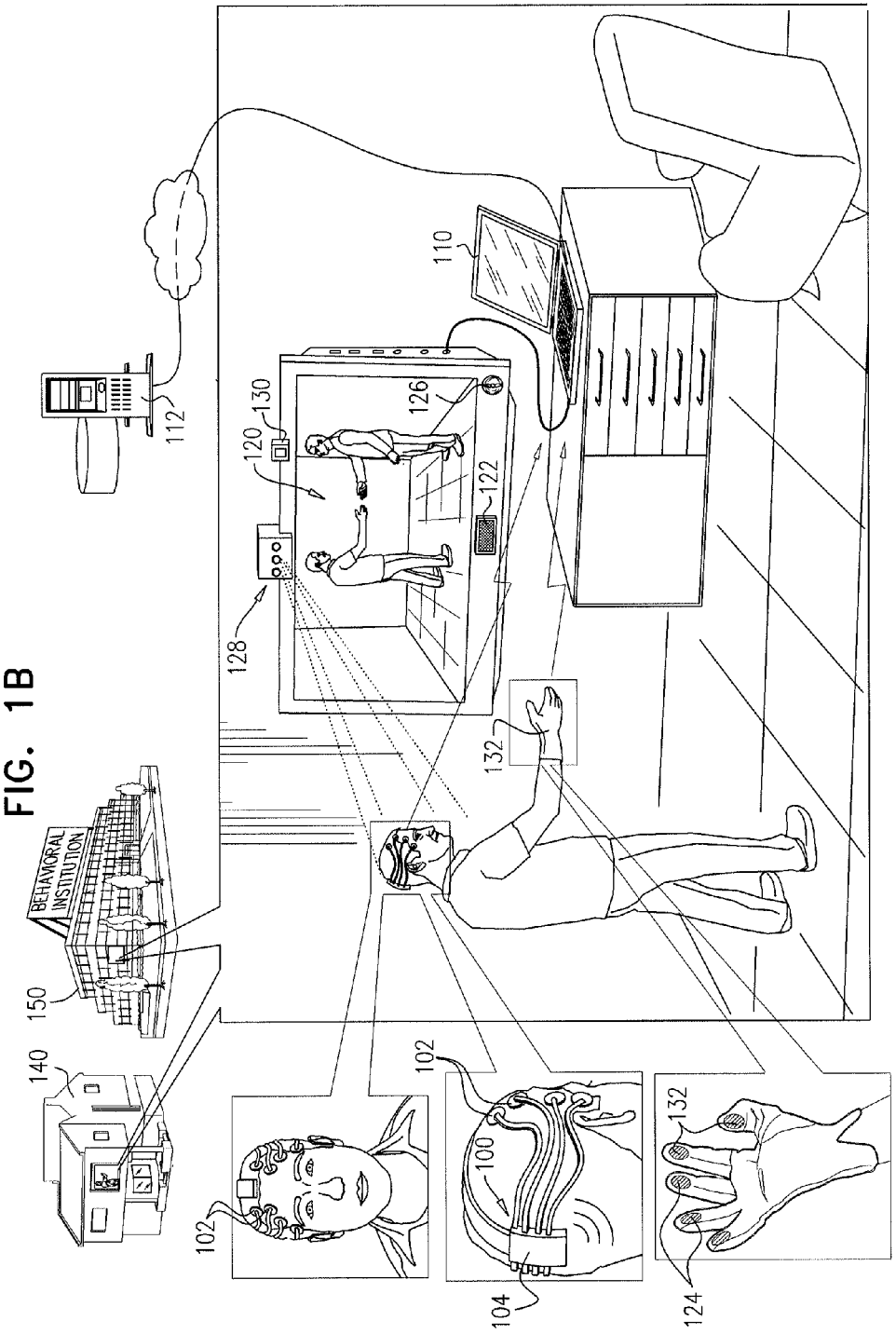
Figure 1C:
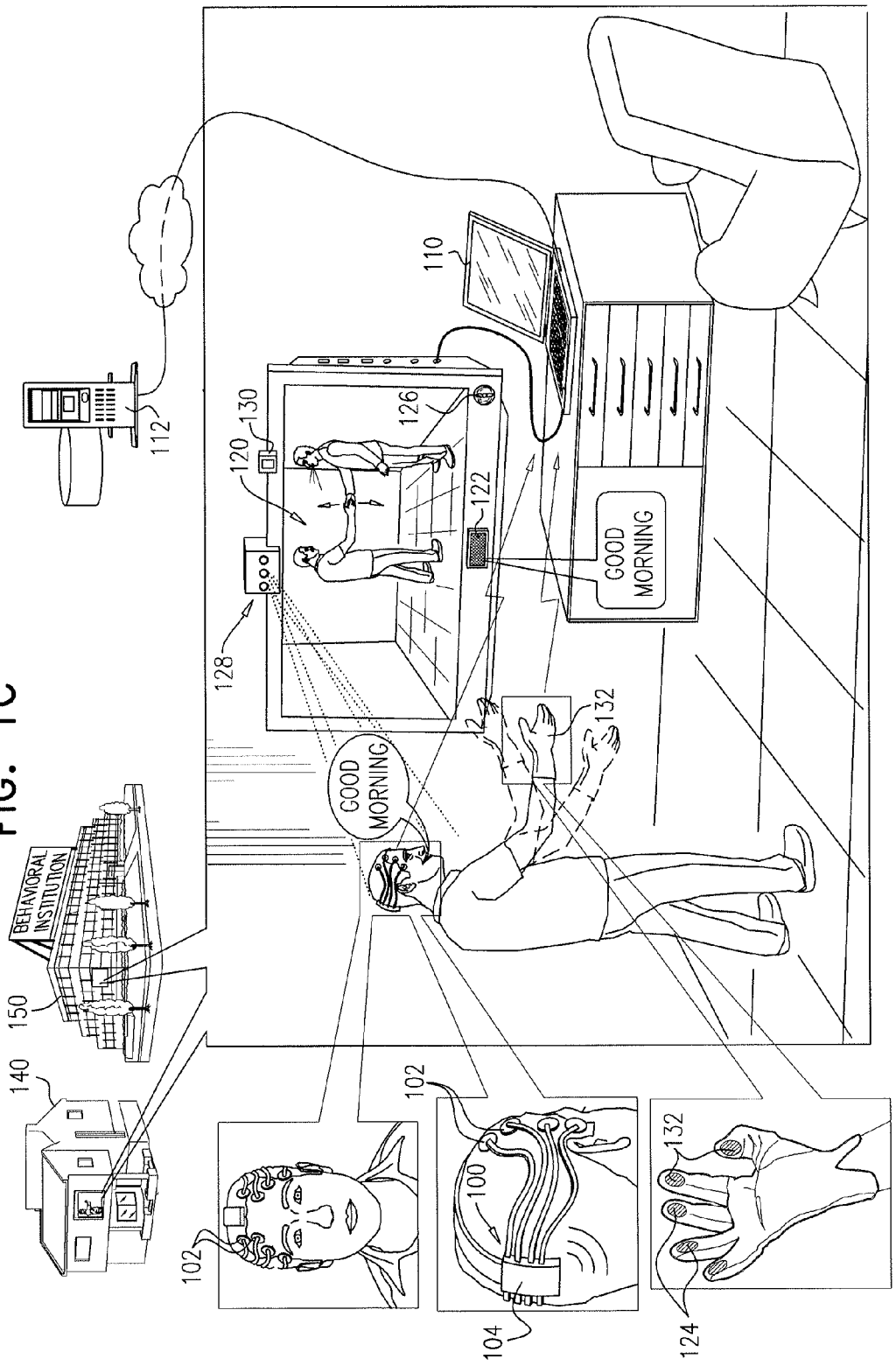

Reference is now made to FIGS. 1A-1C, which illustrate a first typical scenario in the operation of systems and methodologies for neurocognitive training or neuropsychological assessment, constructed and operative in accordance with a preferred embodiment of the present invention.

As seen in FIGS. 1A-1C, a subject is preferably equipped with a brain activity measurement headset 100 which preferably includes a plurality of electrodes 102, preferably including electrodes which measure activity of all of the lobes of the brain. Headset 100 preferably includes a short range wireless transmitter 104 which transmits to a receiver 106, preferably incorporated into or associated with a computer 110 located in the vicinity of the subject. Various types of suitable headsets 100 are commercially available. Examples include: an EPOC neuroheadset commercially available from Emotiv Systems Inc. of San Francisco, Calif., and MindSet from NeuroSky Inc. of San Jose, Calif.

Computer 110 may be any suitable computer which is loaded with wireless signal receiving and preliminary processing and analysis software. Such software is commercially available from Emotiv Systems Inc. of San Francisco, Calif., MindSet from NeuroSky Inc. of San Jose, Calif., as well as other companies.

Computer 110 is preferably connected via a computer network, such as the internet, to one or more remote servers 112, which gather data from multiple neurocognitive interactions with multiple subjects at multiple times. Servers 112 may compile composite data based on the multiple neurocognitive interactions which may be employed in accordance with a preferred embodiment of the invention as inputs in selecting further stimuli to be provided to the subject. The operation of servers 112 may be automatic or may be managed by an operator who may select what data is stored therein and/or what data is made available for use by the system and may modify or annotate that data.

A display device 120 provides desired visual stimuli to the subject and is controlled by computer 110. Optionally, the computer 110 may be incorporated in or associated with the display device 120, such as, for example, where the display device 120 is a conventional television which includes a computer or is associated with a set-top box, which includes a computer. The display device 120 may be any suitable large screen video display screen or projector. Other types of stimulus generators, such as an audio stimulus generator 122, including one or more loudspeakers, a tactile and/or haptic stimulation generator 124, typically mounted on a glove, and an odor stimulus generator 126 may also be provided. The audio stimulus generator 122 is preferably a speaker which is incorporated into a computer or television. Preferred examples of a tactile and/or haptic stimulation generator 124 include CyberTouch, CyberForce and CyberGrasp from CyberGlove Systems LLC, of San Jose, Calif., and PHANTOM Omni from Geomagic (Sensable group), Wilmington, Mass. Preferred examples of an odor stimulus generator 126 include technologies from Scentcom Ltd., Lehavot Haviva, Israel.

A camera 128 and a microphone 130 capture body movements as well as facial and vocal expressions of the subject and provide outputs to computer 110. Preferably computer 110 includes motion sensing software, such as Open NI software from OpenNI, a non-profit organization (http://openni.org/), PrimeSense SDK from PrimeSense Inc of Tel-Aviv, Israel and Kinect SDK from Microsoft Corporation of Redmond, Wash. Camera 128 is preferably a PrimeSense 3D sensor from PrimeSense Inc of Tel-Aviv, Israel, or a Microsoft Kinect camera from Microsoft Corporation of Redmond, Wash. Microphone 130 is preferably integrated into a computer or television or camera. One or more biofeedback sensors 132, such as BioNomadix wireless physiology sensors from BIOPAC Systems Inc., Goleta, Calif., which may include sensors mounted on a glove and on various parts of the subject's body, are preferably also provided and may provide various physiological signals such as respiration, temperature, cardiac output and EMG signals. Sensors associated with headset 100 may also provide biofeedback information. Camera 128, microphone 130 and biofeedback sensors 132 preferably are wirelessly connected to one or more receivers 134 associated with computer 110.

It is appreciated that the above-described system components, with the exception of remote server 112, may readily be transported and located in a subject's home 140 or, alternatively, in an institution, such as a hospital 150 or a rehabilitation center.

Preferably computer 110 includes a neurocognitive training or neuropsychological assessment system core, preferably embodied in software, and including a Behavior and Brain Data Extraction and Analysis Engine 162. Behavior and Brain Data Extraction and Analysis Engine 162 outputs to a Neurocognitive Training and Assessment Logic Engine 164. Engine 164 in turn preferably outputs to a Stimulus Scenario Generator 166, which provides control outputs to the various stimulation apparatus described hereinabove, such as display device 120, loudspeaker 122, tactile and/or haptic stimulation generator 124 and odor stimulus generator 126.

Behavior and Brain Data Extraction and Analysis Engine 162 preferably receives inputs via receivers 106 and 134 from subject data capture apparatus, described hereinabove, such as headset 100, camera 128, microphone 130 and sensors 132, which capture neurofeedback data, biofeedback data, body movements, vocal and facial expressions of the subject. Behavior and Brain Data Extraction and Analysis Engine 162 preferably also receives subject data from a subject data database in computer 110 or in remote server 112 which includes subject profile data and a subject's history of interaction with the system.

Neurocognitive Training or Neuropsychological Assessment Logic Engine 164 receives high level subject action analysis data from Behavior and Brain Data Extraction and Analysis Engine 162 and may also receive subject data from the subject data database in computer 110 or in remote server 112 which includes subject profile data and a subject's history of interaction with the system.

Stimulus Scenario Generator 166 receives stimulus priority instructions from Neurocognitive Training and Assessment Logic Engine 164 and in accordance with its preloaded internal logic, produces stimuli for the subject based thereon and preferably also based on outputs received directly from the Behavior and Brain Data Extraction and Analysis Engine 162 and subject data from the subject data database in computer 110 or in remote server 112 which includes subject profile data and a subject's history of interaction with the system.

It is a particular feature of the present invention that subject data from other subjects, received from a remote server 112, may be employed by any or all of Behavior and Brain Data Extraction and Analysis Engine 162, Neurocognitive Training and Assessment Logic Engine 164 and Stimulus Scenario Generator 166.

FIG. 1A illustrates typical neurocognitive training or assessment interaction wherein the subject sees on the display 120, an image of a person, typically an avatar, who may or may not be similar to the subject, carrying out a desired task. In this case the initial stimulus provided to the subject is a visual stimulus, showing a person extending his hand to a second avatar, who represents the subject.

As seen in FIG. 1B, the subject's response is to extend his hand. This response is captured by camera 128 and represented on display 120 by a similar motion of the avatar.

FIG. 1C shows a further visual stimulus wherein the avatar is seen shaking hands with the person and both the avatar and the person are smiling and the person is speaking. Preferably, this visual stimulus is accompanied by an audio stimulus, provided by audio stimulus generator 122, in which the person says "Good morning!" to the avatar and by a tactile and haptic stimulus, provided by tactile and/or haptic stimulation generator 124, causing the subject to feel a handshake sensation via the glove.

FIG. 1C also shows the subject making a handshake movement and also saying "Good Morning". This movement is preferably captured by camera 128 and by one or more sensors 132 on the glove and the subject's speech is captured by microphone 130.

Reference is now made to FIGS. 2A, 2B, 2C and 2D, which are together a simplified illustration of a second typical scenario in the operation of systems and methodologies for neurocognitive training and/or neuropsychological assessment, constructed and operative in accordance with a preferred embodiment of the present invention.

Figure 2A:
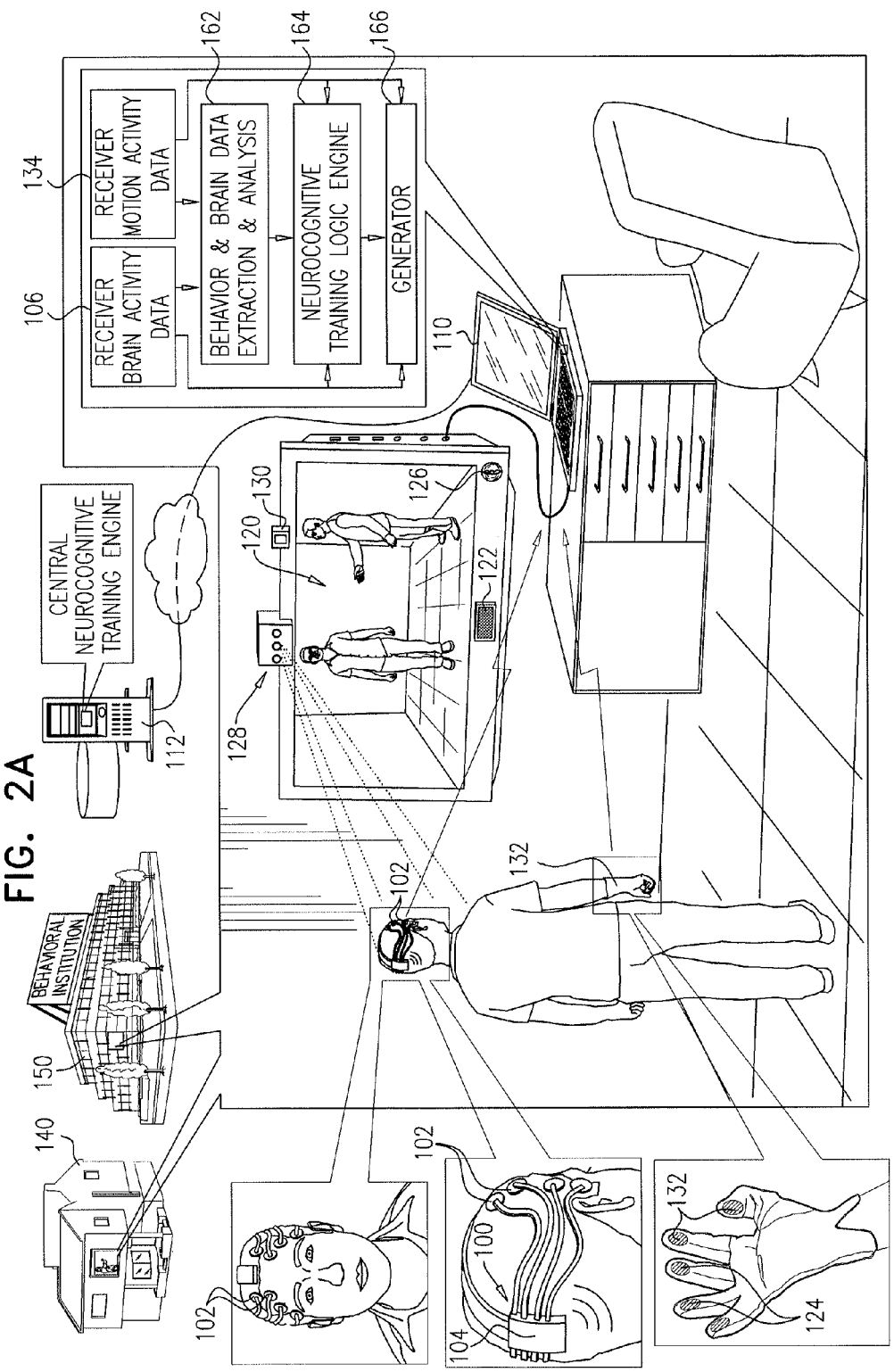
FIGS. 2A, 2B, 2C and 2D are together a simplified illustration of a second typical scenario in the operation of systems and methodologies for neurocognitive interaction, which may be used for assessment and/or training, con-

This second scenario employs the same system as in the first scenario, described hereinabove with reference to FIGS. 1A-1C. In the second scenario, similarly to the first scenario, FIG. 2A illustrates typical neurocognitive training or assessment interaction wherein the subject sees on the display 120, an image of a person, typically an avatar, who may or may not be similar to the subject, carrying out a desired task. In this case the initial stimulus provided to the subject is a visual stimulus, showing a person extending his hand to a second avatar, who represents the subject.

Figure 2B:
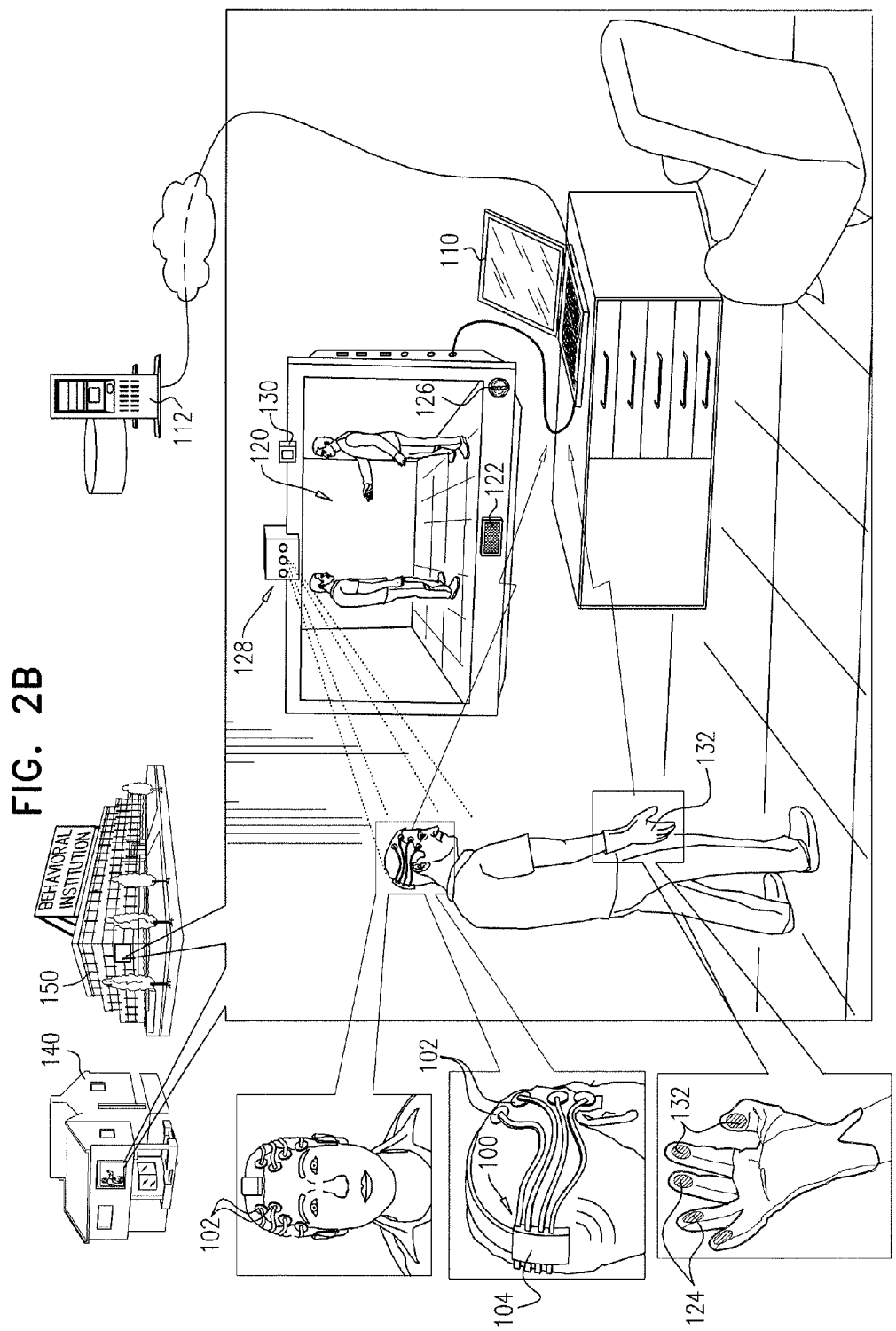

As seen in FIG. 2B, in contrast to the first scenario, the subject does not respond to the stimulus by extending his hand. This lack of response is captured by camera 128 and represented by a similar lack of response of the avatar. Neurofeedback received from headset 100 indicates a lack of interest on the part of the subject.

Figure 2C:
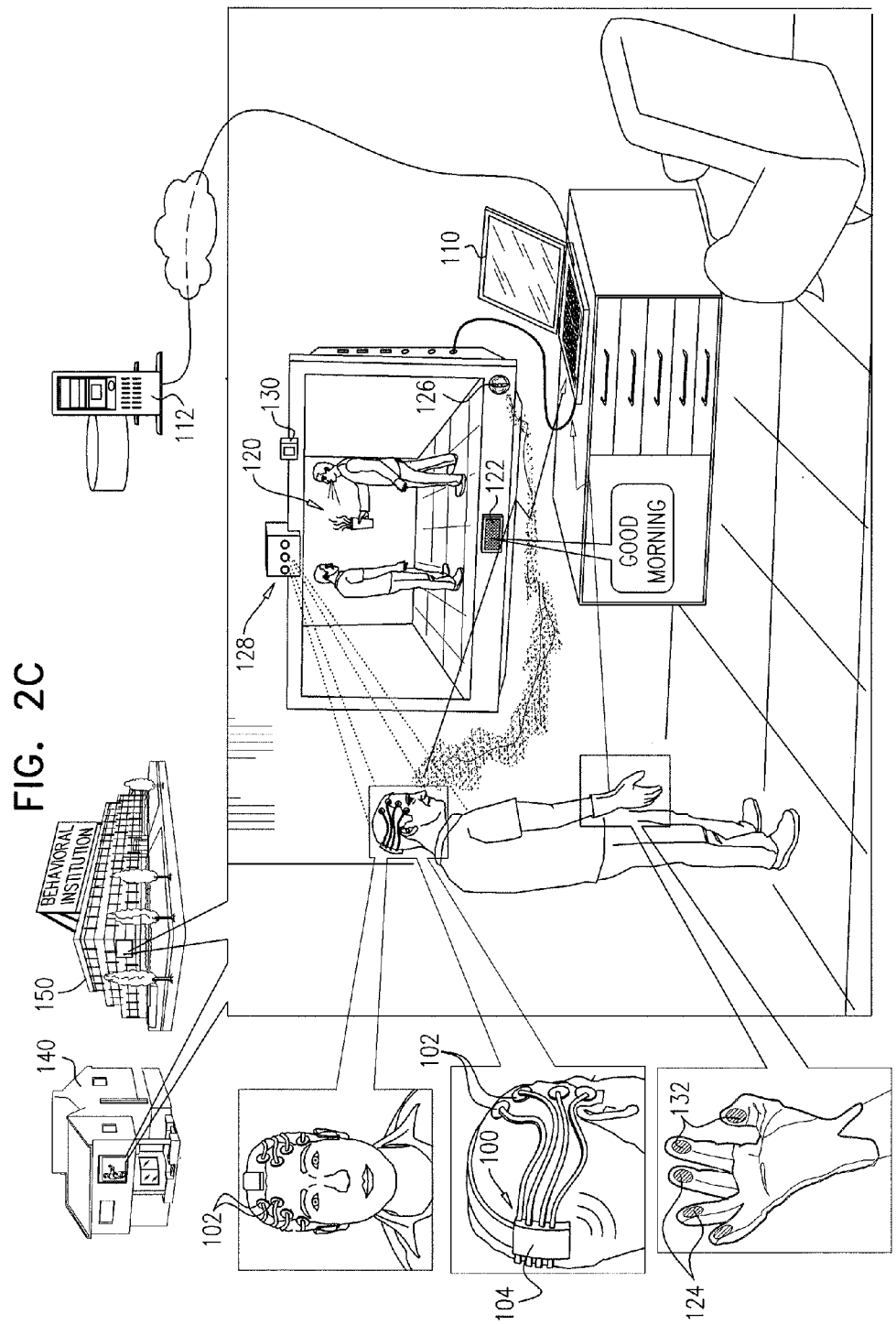

FIG. 2C shows a further visual stimulus wherein the person walks towards the avatar, speaks and offers the avatar a cup of coffee. Preferably, the visual stimulus is accompanied by an audio stimulus, provided by audio stimulus generator 122, in which the person says "Good morning!" to the avatar and by a odor stimulus, provided by odor stimulation generator 126, causing the subject to smell the coffee.

Figure 2D:
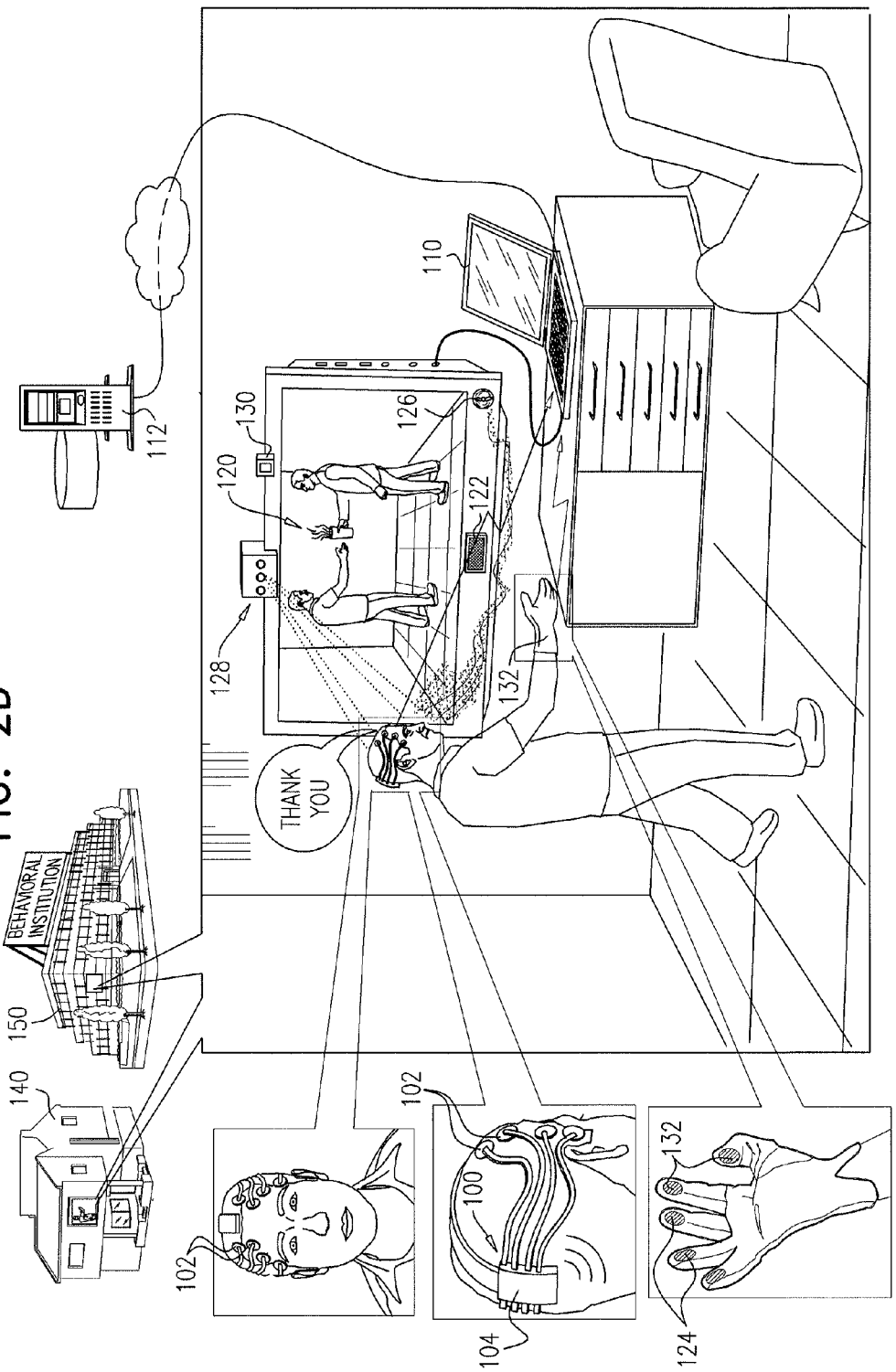

FIG. 2D shows the subject walking towards the person and extending his hand to receive the cup of coffee also saying "Thank you". This movement is preferably captured by camera 128 and by one or more sensors 132 on the glove and the subject's speech is captured by microphone 130.

The scenarios may be constructed interactively based on, inter alia, assessment of the subject's actions in response to earlier stimuli. Preferably, scenarios may be constructed also based on assessment of the subject's brain activity (neurofeedback) and physiological activity (biofeedback) in response to earlier stimuli. The changes to the stimuli may include one or more of the following:

a. the number, duration, timing and/or order of the stimuli;
b. the context in which the stimuli are provided (For example, for visual stimuli, whether the background is indoors or outdoors, whether in bright surroundings or dark surroundings);
c. the type of stimuli (For example, the selection of visual, auditory, olfactory, tactile, haptic or combinations thereof, the selection of still images or moving images);
d. the view which characterizes how the stimuli are experienced (For example, whether a visual stimulus is as seen by the subject or viewing the subject, the extent of zoom, the angle of view;
e. the representation of the subject in the avatar (For example, a real image or an avatar; full body or partial body representation, back or front);
f. the makeup of the environment (e.g. the objects in the environment);
g. the representation of the actions of the subject in the avatar (For example, full or partial mimicking of the behavior of the subject; exaggerated or minimized representation by an avatar of an action by the subject; distortion or directional change in sensed movement of the subject; time delay between subject action and avatar action, the amount of physical action, e.g. extent, speed, direction, of the subject which is required in order to activate a corresponding action of the avatar;
h. the representation of the actions of the subject on the external virtual environment (For example, the amount, e.g. extent, speed, direction, of movement of items in the environment; time delay between subject action and consequential changes in the environment, the amount of physical action, e.g. extent, speed, direction, of the subject which is required in order to activate a corresponding change in the environment, the cause/effect relationship between specific subject actions and resulting changes in the environment;
i. aggressiveness of the stimuli (brightness of a visual stimulus, loudness of an auditory stimulus and more generally strength of a stimulus;
j. extent of interactivity in a scenario initiated by the stimuli (For example, location along a continuum between a non-interactive movie and a fully interactive game; and
k. the representation of one or more physical objects in the stimuli, which objects can be manipulated by the subject (e.g. a remote control device which can be operated by the subject and which may appear virtually as a cup of coffee, a hammer or any other object).

Additionally, the type or extent of subject activity in response to the stimuli which will elicit further given stimuli may be varied. For example, the type, speed, duration and number of subject actions required to elicit a given further stimulus response, such as avatar hand movement, leg movement and speech, may be varied.

The following is a brief description of examples of specific neurocognitive interactions employing the described system and functionality, which may be used for training various neurocognitive functions:

Training response conflict resolution by variable scenarios and gradual challenge Background:

Response conflict resolution, part of executive functions and decision making processes, is an essential cognitive ability which involves choosing between different behavioral options. This ability is impaired in many neurological and mental illnesses involving the frontal lobes, and is sub-optimal in many healthy people. Research and training of this function utilize simple tasks, such as the Stroop task (Colin M. MacLeod "Century of Research on the Stroop Effect: An Integrative Review". Psychological Bulletin 1991, Vol. 109, No. 2, 163-203), where in each trial a stimulus is presented with two aspects of the stimulus indicating two conflicting actions and the user needs to perform only one pre-specified action (e.g. classical word-color Stroop, where the name of a color (red) is printed in an ink of a different color (blue) and the user needs to indicate the color of the ink (blue); the printed word "red" drives attention and therefore causes a response conflict). Since in such paradigms the number of conflicting stimuli aspects is very limited, such training does not address daily life response conflicts where multiple and variable stimuli aspects may induce conflict. Training with a limited number of stimuli leads the subject to optimize attentional processes to specific stimuli aspects (e.g. learn how to focus attention on the color rather than the text) rather that optimize response conflict processes.

Method:

In order to constantly activate and challenge response conflict neural mechanisms the following training method presents a sequence of conflicting situations in one or more of the novel ways described below. Each situation includes a presented stimulus and multiple possible required actions.

The sequence includes multiple different conflicting stimuli settings at each scenario. For example, one scenario with conflict between length and number, another scenario with conflict between color and word, another scenario with conflict between printed and spoken word, another scenario with conflict arrows pointing left and distracter arrows pointing right, etc. The alternation in the conflicting stimuli aspects that are relevant to response-selection forces the subject to learn to optimize response conflict abilities rather than rely on optimizing attentional processes.

Multiple actions and action modalities are required as a response to the scenarios. For example, in one scenario there is conflict between response to move hand to left or the right, in another scenario there is a conflict between saying two different words (e.g. yes and no), in another scenario there is a conflict between saying a word and smiling. The alternation of required action aims to enhance generalization of the training across different behaviors.

Conflict level grows gradually from low conflict. For example, from a low conflict scenario where a target arrow points to the left and all but one distracter arrows point to the same side, to high conflict scenario where the target arrow points left and all distracter arrows point right. Another example: from a low conflict scenario of classical stroop task where the word "red" is written in a reddish-orange color to a high conflict scenario where the word "red" and is written in a green ink. Such a gradual increase in task challenge allows for gradual training of the required cognitive processes of conflict resolution mechanisms.

The above described simple training scenarios may be replaced or alternated with or gradually followed by scenarios that involve more than two action options. For example, arrows in various colors pointing to multiple directions appear on the screen (all red arrows point to right, green point upwards, one blue arrow point to the left, etc.) and the subject needs to press a key corresponding to the direction of arrows of specific color (e.g. blue, thus press left key).

The above described simple training scenarios may be replaced or alternated with or gradually followed by more complex and naturalistic scenarios that require resolution of response conflict. For example, three virtual people asking the subject to do three different actions, or the subject is navigating in a virtual terrain and reaches a point where he needs to choose between several paths. Another example is a scenario where the subject is presented with several conflicting road-signs and needs to choose where to go. The naturalistic scenarios are also presented in multiple environments and target stimuli aspects, as well as with multiple modalities of action (hand motion, body motion, facial expression, etc.). The usage of response conflict situations which are naturalistic as well as multi-modal and multi-context is expected to enhance learning as well as generalization and transfer to daily-life conflict situations.

The selection of scenarios (neurocognitive interactions) to be presented to the subject at each stage will follow the principles described in the invented system (including biofeedback, neurofeedback etc.). The principles described above can be applied also to other neurocognitive functions.

Enhance ability to perform required behaviors or neurocognitive processes by progressive Avatar mirroring Overview:

The following method makes use of the characteristics of the invented system, in particular the ability of the system to manipulate the representation of the actions of the subject in the avatar. In order to enhance the ability to perform required behaviors or neurocognitive processes this method presents, as part of the neurocognitive interaction, a self-avatar, performing behaviors which should be performed by the subject. The subject controls the avatar, causing the avatar to perform the required behavior, however in the beginning the amount of physical action (e.g. extent, speed, effort) which is required by the subject to activate the required (corresponding) action by the avatar may be much smaller (e.g. smaller extent, slower, less effortful) than in the required action and gradually may become more similar to the required action. By letting the subject control and view the required behaviors performed by his avatar, observational learning and mechanisms of imitation and mirroring are employed to induce learning of the required behavior or neurocognitive process. In particular, this method is advantageous for training volitional behaviors and neurocognitive process, for example, self-initiation or empathy and empathetic behavior. Such behaviors are difficult to train using standard stimulus-response training methods paradigms since these paradigms externally trigger subjects for responses and thus do not engage volitional behavior. The application of imitation and mirroring mechanisms allows for training the subjects without externally-triggering them.

Details of Method:

The goal of this method is to reach the situation where the subject is performing some required behavior at relevant scenarios. For example, in training for empathy and empathetic behavior the goal might be to reach a situation where when the subject sees a virtual person in the scenario crying the subject says comforting words to him. Another example, in training to enhance self-initiated behavior, the goal might be to reach a situation where the subject initiates conversations with other virtual people in order to find the way to a desired place, or initiate lifting his hand to reach products on shelves of a virtual supermarket. A preferred protocol to achieve such a goal will start with a scenario where a minimal action (e.g. simple, easy, or even no action) of the player initiates the full required action by the avatar. Which player action is sufficient to induce the full action by the avatar at each stage may be indicated in the scenario via text, visual representation, sound or via any other method. After several events of performance of a minimal player action to induce the full required action, the player is required to perform a more difficult/complex action to induce the required action in the avatar. If he succeeds then a more difficult/complex action is used and so on. If he does not succeed the scenario is repeated with some stimuli to encourage (e.g. hints, instructions) the player to perform the action that will induce the required action in the avatar. This continues until the player is required, and succeeds to perform, the full required action, similarly to the avatar.

For example, in case of training for empathetic behavior—in the beginning the fact that the player comes to stand in front of the virtual crying person causes his avatar to come to the virtual crying person and hug and stroke him, in a later stage in the training the fact that the player comes to the virtual person and lifts his hands will cause his avatar to come and hug and stroke, and so on until eventually at the end of the training the player will need to come, hug and stroke in order for his avatar to do it. In another example of this progression, initially one word of the player causes the avatar to say comforting words to the virtual crying person, yet eventually the player will need to say the comforting word in order for his avatar to say them.

In another example, in the case of training of self-initiation, in the beginning the fact that the player moves his finger causes his avatar to lift both his hands and take some product from a virtual supermarket shelf, in a later stage in the training the fact that the player lifts one hand will cause his avatar to lift both his hands and take the product from the shelf, etc., until eventually at the end of the training the player will need to lift both hands and physically perform the action of taking something from a shelf in order for his avatar to do it. In another example of this progression, initially one word of the player causes the avatar to approach a virtual person to ask for directions, while eventually the player will need to explicitly ask the virtual person for directions in order for his avatar to ask him.

After some specific required actions are learned, the player performs various full required actions (or novel actions) in various contexts, and if he does not perform them then he is trained by the above basic methods to perform the behavior in this context. This description presents the major principles of this method; other specific embodiments using these principles may also be used in a similar way.

Training sensitivity to reward and sensitivity to effort by progressively changing scenarios Background:

The proposed method aims to modulate sensitivity to reward and/or effort. Neurological and psychiatric disorders often lead to reduced sensitivity to reward, where patients are less attracted by rewards and do not act to receive them. In addition, these disorders also may lead to increased sensitivity to effort thereby patients perceive tasks as very effortful and therefore refrain from initiating behaviors. Thus, for people who are less sensitive to rewards the goal is to increase their sensitivity to receiving rewards, by causing them to act more than they used to for smaller rewards. For people who are over sensitive to effort, the goal is to reduce their sensitivity to effort, meaning to cause them to act when it requires higher efforts. Long-term, such training approach aims to cause people to be more sensitive to rewards (in their detection, in the enjoyment from them, and in wanting them) and less sensitive to the efforts.

Method:

For effort sensitivity: A preferred protocol includes scenarios which lead or encourage the subject to initiate actions involving effort, where the level of effort gradually increases during each session and from session to session. Thus, at the beginning the scenarios require very easy actions and gradually to achieve the same results the subject will need to invest more and more effort.

For reward sensitivity: A preferred protocol includes scenarios which lead or encourage the subject to initiate actions for receiving rewards, where the level of reward received for a given action gradually decreases during each session and from session to session. Thus, the stimuli gradually transition from highly motivating stimuli (on a personal level) to stimuli that elicit less motivation in the subject.

The two above protocols may also be combined and implemented concomitantly, where reward gradually decreases and effort increases in parallel. This gradual decrease/increase is implemented by dynamical adjustment of effort, rewarding stimuli and actions to participant's preferences and behavior. Thus, for every modification of reward effort or action the performance of the player is inspected and at the next stage an adjustment is made accordingly. Although overall effort will increase and/or reward will decrease for initiated action, from time to time scenarios which require an action with lower effort and/or provide higher reward are inserted to the protocol. This is done in order to maintain user motivation and engagement and/or for assessment purposes.

Example:

The environment contains many objects and on each object there is an indication which actions on this object will lead the user towards the treasure (reward). The player can move his hands freely in the virtual terrain and decide whether and which actions to perform that lead to the treasure, if the user doesn't initiate any action, the required actions on the objects will become easier or change to better match the preferences of the participant, until the participant acts, and his action will be rewarded. Following receiving the reward the scenario continues, but now with a more challenging action/reward ratio (either the effort of the actions is slightly higher or the reward is a bit lower), which may be dynamically changed when the participant does not act.

Enhancement of self-initiation by initiation-inducing scenarios

Background:

Many neurological and psychiatric disorders lead to impairment in performing self-initiated purposeful behavior (termed apathy; Richard Levy and Bruno Dubois, "Apathy and the Functional Anatomy of the Prefrontal Cortex—Basal Ganglia Circuits." Cerebral Cortex 2006; 16:916-928). A major challenge in training to enhance self-initiation is that standard trial-based methods, which are the common methods in computerized training, externally trigger action. This, paradoxically, does not engage self-initiation mechanisms since the user is triggered to initiate and act.

Method:

In the proposed method to enhance self-initiated behavior, the user is introduced to scenarios which encourage initiation of specific actions, although not explicitly triggering for action. Exposing the user to such scenarios can train the user to initiate various types of behaviors in various situations. An initiation-inducing scenario may be one where the user is presented with some goal he needs to achieve (e.g. find flowers and pick them), but the actions to achieve this goal and their timing are not specified exactly by the environment. The level at which the actions are specified (will be termed here the level of external-triggering of the environment) can be varied. Thus, higher levels of triggering are generally more likely to trigger action initiation (a flashing red flower is shown on the screen), whereas initiation of action in scenarios with lower levels of triggering (no flower is seen and the user needs to move bushes in the forest to find the flowers) are generally less likely and thus it is the aim of this training to induce self-initiated action. In the basic training, an initiation-inducing scenario is presented, and if the required action is not initiated by the user, the environment is adjusted to further promote action initiation (triggering is increased). If the required action is initiated, then the triggering level is decreased. This process is repeated until initiation is performed in the lowest level of triggering. In addition to this basic method, additional information about behavior (e.g. body movements, facial expressions, speech) and brain activity (e.g. EEG waves or ERPs) are used to better adjust the environment to generate initiation-inducing environments. For example, if the system detects that the user did not perform the required action, but he is attentive, as indicated by the beta waves measured on his scalp, then the triggering level is increased. If the user is not attentive, the triggering type may be changed, for example, if the previous trigger was a spotlight on the bushes hiding the flower, a new trigger may be movement of the respective bushes, or a small bird flying near the bush. This process is repeated until initiation is performed with the lowest level of triggering.

Similarly, initiation-inducing scenarios can be optimized based on behavioral feedback. For example, if the required action is not performed but the system, using the motion sensor, detected that another, incorrect, action was performed, this may indicate that the user is capable of initiation at this triggering level, but needs to be directed to the right action, thus the subsequent trigger will be more focused. For example, if the previous trigger was moving the bushes on the left-top side of the screen, indicating that the flower is behind them, the current trigger may be to move a specific bush on the screen. If, however, the required action is not performed and no other action is performed, then, for example, the type of triggering may be changed and the level of triggering may be decreased.

The above described methods, and more complex versions thereof, may be combined with each other and with other methods. These examples are for the purpose of illustration of the principles, and are not limiting in any way.

It will be appreciated by persons skilled in the art that the present invention is not limited by what has been particularly shown and described hereinabove. Rather the present invention includes both combinations and subcombinations of various features described herein and improvements and variations which would occur to persons skilled in the art upon reading the foregoing description and which are not in the prior art.

The invention claimed is:

1. A method for neurocognitive training or neuropsychological assessment of a subject comprising:
   providing a computer including a processor which is loaded with software configured and operable to:
      assess at least one initial action of said subject in response to said at least one initial stimulus provided to the subject, said at least one initial action being at least one of absence, presence, timing and/or form of at least one of body movements, vocal expressions and facial expressions;
      based on said assessing said at least one initial action of said subject in response to said at least one initial stimulus, thereafter provide at least one further stimulus to said subject;
      assess at least one further action of said subject in response to said at least one further stimulus, said at least one further action being at least one of absence, presence, timing and/or form of at least one of body movements, vocal expressions and facial expressions; and
      based at least on said assessing said at least one further action of said subject in response to said at least one further stimulus, thereafter provide at least one additional stimulus to said subject;
   wherein said at least one further stimulus differs from said at least one initial stimulus in the following respects:
      a representation of the actions of the subject in the stimuli;
      a representation of one or more physical objects in the stimuli,
   wherein when the objects undergo manipulation by the subject, the manipulation is represented in the stimuli,
   wherein additional information about brain activity including at least one of EEG waves and ERPs is used to generate an initiation-inducing environment, including:
   increasing a triggering level when the system detects that the subject did not perform the required action, but is attentive, as indicated by at least one electrophysiological measurement; and
   changing the triggering type when the system detects that the subject is not attentive.

2. The computer implemented method of neurocognitive training or neuropsychological assessment of a subject according to claim 1 and wherein said assessment employs neurofeedback.

3. The computer implemented method of neurocognitive training or neuropsychological assessment of a subject according to claim 1 and wherein said at least one further stimulus differs from said at least one initial stimulus in at least five of the following respects:
   a. the number, duration, timing and/or order of the stimuli;
   b. the context in which the stimuli are provided;
   c. the type of stimuli;
   d. the view which characterizes how the stimuli are experienced;
   e. the representation of the subject in the stimuli;
   f. the makeup of the environment of the stimuli;
   g. the representation of the actions of the subject in the stimuli;
   h. the representation of the actions of the subject on an external virtual environment;
   i. aggressiveness of the stimuli;

j. extent of interactivity in a scenario initiated by the stimuli; and
k. the representation of one or more physical objects in the stimuli, which objects can be manipulated by the subject.

4. The computer implemented method of neurocognitive training or neuropsychological assessment of a subject according to claim 1 and wherein said at least one further stimulus differs from said at least one initial stimulus in all of the following respects:
   a. the number, duration, timing and/or order of the stimuli;
   b. the context in which the stimuli are provided;
   c. the type of stimuli;
   d. the view which characterizes how the stimuli are experienced;
   e. the representation of the subject in the stimuli;
   f. the makeup of the environment of the stimuli;
   g. the representation of the actions of the subject in the stimuli;
   h. the representation of the actions of the subject on an external virtual environment;
   i. aggressiveness of the stimuli;
   j. extent of interactivity in a scenario initiated by the stimuli; and
   k. the representation of one or more physical objects in the stimuli, which objects can be manipulated by the subject.

5. The computer implemented method of neurocognitive training or neuropsychological assessment of a subject according to claim 1 and wherein at least one of the type and extent of subject activity in response to said at least one initial stimulus which will elicit a given at least one further stimulus is variable.

6. The computer implemented method of neurocognitive training or neuropsychological assessment of a subject according to claim 2 and wherein said at least one further stimulus differs from said at least one initial stimulus in at least five of the following respects:
   a. the number, duration, timing and/or order of the stimuli;
   b. the context in which the stimuli are provided;
   c. the type of stimuli;
   d. the view which characterizes how the stimuli are experienced;
   e. the representation of the subject in the stimuli;
   f. the makeup of the environment of the stimuli;
   g. the representation of the actions of the subject in the stimuli;
   h. the representation of the actions of the subject on an external virtual environment;
   i. aggressiveness of the stimuli;
   j. extent of interactivity in a scenario initiated by the stimuli; and
   k. the representation of one or more physical objects in the stimuli, which objects can be manipulated by the subject.

7. The computer implemented method of neurocognitive training or neuropsychological assessment of a subject according to claim 2 and wherein said at least one further stimulus differs from said at least one initial stimulus in all of the following respects:
   a. the number, duration, timing and/or order of the stimuli;
   b. the context in which the stimuli are provided;
   c. the type of stimuli;
   d. the view which characterizes how the stimuli are experienced;
   e. the representation of the subject in the stimuli;
   f. the makeup of the environment of the stimuli;
   g. the representation of the actions of the subject in the stimuli
   h. the representation of the actions of the subject on an external virtual environment;
   i. aggressiveness of the stimuli;
   j. extent of interactivity in a scenario initiated by the stimuli; and
   k. the representation of one or more physical objects in the stimuli, which objects can be manipulated by the subject.

8. The computer implemented method of neurocognitive training or neuropsychological assessment of a subject according to claim 2 and wherein at least one of the type and extent of subject activity in response to said at least one initial stimulus which will elicit a given at least one further stimulus is variable.

9. The computer implemented method of neurocognitive training or neuropsychological assessment of a subject according to claim 1, wherein said at least one further stimulus provided to said subject differs from said at least one initial stimulus in respect of at least one of:
   a representation of said subject in an avatar in said at least one further stimulus; and
   a representation of at least one action of said subject in said avatar in said at least one further stimulus.

10. The computer implemented method of neurocognitive training or neuropsychological assessment of a subject according to claim 9 and wherein said assessing employs at least one of neurofeedback and biofeedback.

11. The computer implemented method of neurocognitive training or neuropsychological assessment of a subject according to claim 9 and wherein said at least one further stimulus also differs from said at least one initial stimulus in at least one of the following respects:
   the number, duration, timing and/or order of the stimuli;
   the context in which the stimuli are provided;
   the type of stimuli;
   the makeup of an environment of the stimuli;
   aggressiveness of the stimuli;
   extent of interactivity in a scenario initiated by the stimuli; and
   the representation of one or more physical objects in the stimuli, which objects can be manipulated by the subject.

12. The computer implemented method of neurocognitive training or neuropsychological assessment of a subject according to claim 9 and wherein said at least one further stimulus also differs from said at least one initial stimulus in at least three of the following respects:
   the number, duration, timing and/or order of the stimuli;
   the context in which the stimuli are provided;
   the type of stimuli;
   the makeup of an environment of the stimuli;
   aggressiveness of the stimuli;
   extent of interactivity in a scenario initiated by the stimuli; and
   the representation of one or more physical objects in the stimuli, which objects can be manipulated by the subject.

13. The computer implemented method of neurocognitive training or neuropsychological assessment of a subject according to claim 9 and wherein said at least one further stimulus also differs from said at least one initial stimulus in all of the following respects:
   the number, duration, timing and/or order of the stimuli;
   the context in which the stimuli are provided;
   the type of stimuli;

the makeup of an environment of the stimuli;
aggressiveness of the stimuli;
extent of interactivity in a scenario initiated by the stimuli; and
the representation of one or more physical objects in the stimuli, which objects can be manipulated by the subject.

14. The computer implemented method of neurocognitive training or neuropsychological assessment of a subject according to claim 9 and wherein at least one of the type and extent of subject activity in response to said at least one initial stimulus which will elicit a given at least one further stimulus is variable.

15. The computer implemented method of neurocognitive training or neuropsychological assessment of a subject according to claim 10 and wherein said at least one further stimulus also differs from said at least one initial stimulus in at least one of the following respects:
the number, duration, timing and/or order of the stimuli;
the context in which the stimuli are provided;
the type of stimuli;
the makeup of an environment of the stimuli;
aggressiveness of the stimuli;
extent of interactivity in a scenario initiated by the stimuli; and
the representation of one or more physical objects in the stimuli, which objects can be manipulated by the subject.

16. The computer implemented method of neurocognitive training or neuropsychological assessment of a subject according to claim 10 and wherein said at least one further stimulus also differs from said at least one initial stimulus in at least three of the following respects:
the number, duration, timing and/or order of the stimuli;
the context in which the stimuli are provided;
the type of stimuli;
the makeup of an environment of the stimuli;
aggressiveness of the stimuli;
extent of interactivity in a scenario initiated by the stimuli; and
the representation of one or more physical objects in the stimuli, which objects can be manipulated by the subject.

17. The computer implemented method of neurocognitive training or neuropsychological assessment of a subject according to claim 10 and wherein said at least one further stimulus also differs from said at least one initial stimulus in all of the following respects:
the number, duration, timing and/or order of the stimuli;
the context in which the stimuli are provided; the type of stimuli;
the makeup of an environment of the stimuli;
aggressiveness of the stimuli;
extent of interactivity in a scenario initiated by the stimuli; and
the representation of one or more physical objects in the stimuli, which objects can be manipulated by the subject.

18. The computer implemented method of neurocognitive training or neuropsychological assessment of a subject according to claim 10 and wherein at least one of the type and extent of subject activity in response to said at least one initial stimulus which will elicit a given at least one further stimulus is variable.

19. The computer implemented method according to claim 9 wherein said at least one further stimulus also differs from said at least one initial stimulus in respect of at least one of:
a view which characterizes how said at least one further stimulus is experienced; and
a representation of at least one action of said subject.

20. The computer implemented method according to claim 1 wherein said at least one further stimulus differs from said at least one initial stimulus in at least the following respect: the direction of a subject's physical action required in order to activate a corresponding change in the environment.

21. The computer implemented method according to claim 1 wherein said at least one further stimulus differs from said at least one initial stimulus in at least the following respect: extent of interactivity in a scenario initiated by the stimuli.

22. The computer implemented method of neurocognitive training or neuropsychological assessment of a subject according to claim 1 and wherein said assessment employs biofeedback.

23. The computer implemented method according to claim 1, wherein said at least one further stimulus also differs from said at least one initial stimulus in at least one of the following respects:
a view which characterizes how the stimuli are experienced;
a representation of the subject in the stimuli;
makeup of an environment of the stimuli;
a representation of the actions of the subject on an external virtual environment;
aggressiveness of the stimuli; and
extent of interactivity in a scenario initiated by the stimuli.

24. A system for neurocognitive training or neuropsychological assessment of a subject comprising:
a computer which is loaded with software configured and operable to:
assess at least one initial action of the subject in response to at least one initial stimulus provided to the subject, said at least one initial action being at least one of absence, presence, timing and/or form of at least one of body movements, vocal expressions and facial expressions;
based on said assessing said at least one initial action of said subject in response to said at least one initial stimulus, thereafter provide at least one further stimulus to said subject;
assess at least one further action of said subject in response to said at least one further stimulus, said at least one further action being at least one of absence, presence, timing and/or form of at least one of body movements, vocal expressions and facial expressions; and
based at least on said assessing said at least one further action of said subject in response to said at least one further stimulus, thereafter provide at least one additional stimulus to said subject;
wherein said at least one further stimulus differs from said at least one initial stimulus in the following respects:
a representation of the actions of the subject in the stimuli; and
a representation of one or more physical objects in the stimuli, and
wherein when the objects undergo manipulation by the subject the manipulation is represented in the stimuli, wherein additional information about brain activity including at least one of EEG waves and ERPs is used to generate an initiation-inducing environment, including:
  increasing a triggering level when the system detects that the subject did not perform the required action, but is attentive, as indicated by at least one electrophysiological measurement; and
  changing the triggering type when the system detects that the subject is not attentive.

25. The system according to claim 24, further comprising a brain activity measurement headset to measure activity of a brain of the subject.

26. The system according to claim 24, wherein the stimulus output device comprises a display to provide the at least one initial stimulus, the at least one further stimulus and the at least one additional stimulus to the subject.

27. The system according to claim 26, wherein the stimulus output device further comprises at least one of an audio stimulus generator, a tactile stimulation generator, a haptic stimulation generator and an odor stimulus generator.

28. The system according to claim 24, further comprising a camera and a microphone connected to the computer to capture data representing body movements, facial expressions, and vocal expressions of the subject and output the data to the computer.

29. A system for neurocognitive training or neuropsychological assessment of a subject comprising:
  a computer comprising a processor, a computer readable memory connected to the processor, and a stimulus output device connected to the processor, the computer readable memory storing software configured and operable to:
    output at least one initial stimulus via the stimulus output device to said subject, the at least one initial stimulus comprising an avatar carrying out a desired task;
    assess at least one initial action of the subject in response to the at least one initial stimulus provided to the subject, said at least one initial action being at least one of absence, presence, timing and/or form of at least one of body movements, vocal expressions and facial expressions;
    based on said assessing said at least one initial action of said subject in response to said at least one initial stimulus, thereafter provide at least one further stimulus to said subject;
    assess at least one further action of said subject in response to said at least one further stimulus, said at least one further action being at least one of absence, presence, timing and/or form of at least one of body movements, vocal expressions and facial expressions; and
    based at least on said assessing said at least one further action of said subject in response to said at least one further stimulus, thereafter provide at least one additional stimulus to said subject;
  wherein the at least one further stimulus and the at least one additional stimulus are constructed based on the assessing performed in response to earlier stimuli,
  wherein said at least one further stimulus differs from said at least one initial stimulus in the following respects:
    a representation of the actions of the subject in the stimuli; and
    a representation of one or more physical objects in the stimuli, and
  wherein when the objects undergo manipulation by the subject the manipulation is represented in the stimuli,
  wherein additional information about brain activity including at least one of EEG waves and ERPs is used to generate an initiation-inducing environment, including:
    increasing a triggering level when the system detects that the subject did not perform the required action, but is attentive, as indicated by at least one electrophysiological measurement; and
    changing the triggering type when the system detects that the subject is not attentive.

* * * * *